US005815182A

United States Patent [19]

Otis et al.

[11] Patent Number: 5,815,182

[45] Date of Patent: Sep. 29, 1998

[54] FLUID INTERCONNECT FOR INK-JET PEN

[75] Inventors: David R. Otis, Corvallis, Oreg.; Ngoc-Diep T. Nguyen, Vancouver; Thomas G. Cocklin, Ridgefield, both of Wash.; John G. Wydronek, Corvallis, Oreg.

[73] Assignee: Hewlett-Packard Company, Palo Alto, Calif.

[21] Appl. No.: 566,985

[22] Filed: Dec. 4, 1995

[51] Int. Cl.[6] ............................ B41J 2/175; A61B 17/43

[52] U.S. Cl. ............................... 347/85; 347/86; 604/905

[58] Field of Search ........................ 347/85, 86; 604/283, 604/86, 256, 905; 251/149.1, 149.6; 346/140 R, 1.1, 75

[56] References Cited

U.S. PATENT DOCUMENTS

| | | |
|---|---|---|
| 594,196 | 11/1897 | Cramer . |
| 714,264 | 11/1902 | Turajski . |
| 743,798 | 11/1903 | Allwardt . |
| 1,150,420 | 8/1915 | Davis . |
| 1,304,814 | 5/1919 | Schweinert . |
| 1,451,037 | 4/1923 | Blanchard . |
| 1,563,331 | 12/1925 | Bright . |
| 1,588,898 | 6/1926 | Martocello . |
| 1,638,488 | 8/1927 | Kellogg . |
| 1,759,872 | 5/1930 | Schwimmer . |
| 1,767,391 | 6/1930 | Muller . |
| 1,850,879 | 3/1932 | Hunt . |
| 1,859,018 | 5/1932 | Bedford . |
| 1,918,602 | 7/1933 | Joyce . |
| 2,011,639 | 8/1935 | Johannesson . |
| 2,024,682 | 12/1935 | Eisenman . |
| 2,086,569 | 7/1937 | Meyer . |
| 2,092,116 | 9/1937 | Hansen . |
| 2,258,919 | 10/1941 | Wallace . |
| 2,265,267 | 12/1941 | Cowles . |
| 2,288,565 | 6/1942 | Green . |
| 2,327,611 | 8/1943 | Scheiwer . |
| 2,370,182 | 2/1945 | Morrow . |
| 2,373,886 | 4/1945 | Geiger . |
| 2,412,685 | 4/1946 | Hoffman et al. . |
| 2,434,167 | 1/1948 | Knoblauch . |
| 2,459,477 | 1/1949 | Schuyver . |
| 2,492,271 | 12/1949 | Cox . |
| 2,557,807 | 6/1951 | Wagner . |
| 2,598,009 | 5/1952 | Peeps . |
| 2,612,389 | 9/1952 | MacGlashan . |
| 2,727,759 | 12/1955 | Elliott . |
| 2,789,838 | 4/1957 | Palm . |
| 2,842,382 | 7/1958 | Franck . |
| 2,888,173 | 5/1959 | Wolcott . |
| 2,915,325 | 12/1959 | Foster . |
| 2,919,935 | 1/1960 | Nyberg . |
| 2,925,103 | 2/1960 | Kerr . |
| 3,102,770 | 9/1963 | McKeegan . |
| 3,104,088 | 9/1963 | Cator . |
| 3,106,379 | 10/1963 | Sciuto . |
| 3,140,912 | 7/1964 | Davis . |
| 3,152,452 | 10/1964 | Bond, Jr. . |

(List continued on next page.)

*Primary Examiner*—Peter S. Wong
*Assistant Examiner*—Rajnikant B. Patel

[57] ABSTRACT

A fluid interconnect connects an ink pen to a carriage on an ink-jet printer. The ink pen has an inlet assembly having a septum. The carriage has an outlet assembly that includes a collar and a needle with a lateral hole. The inlet assembly is insertable into the outlet assembly to move the collar from a closed position, in which the collar covers the lateral hole, into an open position, in which the lateral hole is exposed within the inlet assembly, to allow ink to flow through the outlet assembly into the inlet assembly. The septum occludes fluid flow from the inlet assembly when the inlet and outlet assemblies are uncoupled. The septum has a blister that seals the inlet assembly against the outlet assembly when the inlet and outlet assemblies are coupled. The inlet assembly also has a ridge for attracting, by capillary attraction, any fluid that may escape from the interconnect.

22 Claims, 2 Drawing Sheets

U.S. PATENT DOCUMENTS 3,157,314 11/1964 Nadler .
3,170,667 2/1965 Szohatzky .
3,223,117 12/1965 Curie .
3,230,964 1/1966 Debrotnic .
3,279,497 10/1966 Norton .
3,339,883 9/1967 Drake .
3,359,015 12/1967 Zahuranec .
3,430,824 3/1969 Conners .
3,490,473 1/1970 Ehrens .
3,493,146 2/1970 Conners .
3,537,477 11/1970 Mahoff .
3,613,959 10/1971 Mason .
3,614,940 10/1971 Abrams et al. .
3,640,309 2/1972 Demler, Sr. .
3,708,798 1/1973 Hildenbrand .
3,777,771 12/1973 De Visscher .
3,777,782 12/1973 Shendure .
3,787,882 1/1974 Fillmore .
3,805,276 4/1974 Ishii .
3,825,222 7/1974 Petrova .
3,831,727 8/1974 Kruspe .
3,873,062 3/1975 Johnson .
3,896,853 7/1975 Bernhard .
3,924,654 12/1975 Buller .
3,929,071 12/1975 Cialone et al. .
3,950,761 4/1976 Kashio .
3,961,337 6/1976 Jung .
4,053,901 10/1977 Skafvenstedt .
4,053,902 10/1977 Skafvenstedt .
4,074,284 2/1978 Dexter .
4,079,384 3/1978 Takano .
4,084,165 4/1978 Skafvenstedt .
4,114,853 9/1978 Medvick .............................. 251/149.6
4,119,034 10/1978 Wax .
4,122,457 10/1978 Erickson .
4,126,868 11/1978 Kirner .
4,131,899 12/1978 Christou .
4,142,653 3/1979 Mascia .
4,149,172 4/1979 Heinzl .
4,156,244 5/1979 Erickson .
4,162,501 7/1979 Mitchell et al. .
4,178,595 12/1979 Jinnai .
4,183,031 1/1980 Kyser .
4,187,511 2/1980 Robinson .
4,204,215 5/1980 Nakarai .
4,234,885 11/1980 Arway .
4,253,103 2/1981 Heinzl .
4,263,602 4/1981 Matsumoto .
4,270,133 5/1981 Shimazawa .
4,287,523 9/1981 Thomas .
4,303,929 12/1981 Blanck .
4,320,407 3/1982 Goldis .
4,323,907 4/1982 Italiano .
4,324,239 4/1982 Gordon .
4,329,698 5/1982 Smith .
4,339,761 7/1982 Matsumoto .
4,340,896 7/1982 Cruz-Uribe .
4,342,041 7/1982 Kasugayama .
4,342,042 7/1982 Cruz-Uribe .
4,345,627 8/1982 Cassia .
4,357,617 11/1982 Shimazawa .
4,371,004 2/1983 Sysolin .
4,376,283 3/1983 Bower .
4,380,772 4/1983 Italiano .
4,383,263 5/1983 Ozawa .
4,394,669 7/1983 Ozawa .
4,403,229 9/1983 Bartek .
4,412,232 10/1983 Weber .
4,413,267 11/1983 Hein .
4,419,677 12/1983 Kasugayama .
4,419,678 12/1983 Kasugayama et al. .
4,421,296 12/1983 Stephens .
4,422,084 12/1983 Saito .
4,422,086 12/1983 Miura .
4,429,320 1/1984 Hattori .
4,433,341 2/1984 Thomas .
4,447,820 5/1984 Terasawa .
4,456,916 6/1984 Kocot .
4,460,904 7/1984 Oszczakiewicz .
4,462,037 7/1984 Bangs .
4,471,364 9/1984 Kocot .
4,475,116 10/1984 Sicking .
4,476,472 10/1984 Aiba .
4,496,959 1/1985 Frerichs .
4,496,960 1/1985 Fischbeck .
4,498,658 2/1985 Mikiya .
4,500,895 2/1985 Buck .
4,502,059 2/1985 Blessington .
4,506,862 3/1985 Spinosa .
4,509,659 4/1985 Cloutier .
4,511,906 4/1985 Hara .
4,520,369 5/1985 Shackleton .
4,527,170 7/1985 Iwasaki .
4,527,175 7/1985 Kojima .
4,536,777 8/1985 Matsumoto .
4,541,457 9/1985 Blenkush .
4,542,386 9/1985 Delligatii .
4,542,390 9/1985 Bruning .
4,555,719 11/1985 Arway .
4,558,326 12/1985 Kimura .
4,568,954 2/1986 Rosback .
4,575,738 3/1986 Sheufelt .
4,576,199 3/1986 Svensson .
4,586,058 4/1986 Yamazaki .
4,590,494 5/1986 Ichihashi .
4,591,875 5/1986 McCann .
4,593,294 6/1986 Parisi .
4,599,625 7/1986 Terasawa .
4,600,927 7/1986 Sugitani .
4,602,662 7/1986 Eremity .
4,604,633 8/1986 Kimura .
4,607,261 8/1986 McCann .
4,609,925 9/1986 Nozu .
4,610,202 9/1986 Ebimura .
4,623,905 11/1986 Ichibashi .
4,628,332 12/1986 Matsumoto .
4,628,333 12/1986 Terasawa .
4,630,072 12/1986 Scardovi .
4,630,758 12/1986 Mutoh .
4,636,814 1/1987 Terasawa .
4,639,738 1/1987 Young .
4,658,272 4/1987 Toganoh .
4,658,273 4/1987 Yuki .
4,672,993 6/1987 Bilak .
4,673,955 6/1987 Ameyama .
4,677,447 6/1987 Nielsen .
4,680,696 7/1987 Ebinuma .
4,683,905 8/1987 Vigneau .
4,684,962 8/1987 Hirosawa .
4,689,642 8/1987 Sugitani .
4,694,307 9/1987 Toganoh .
4,695,824 9/1987 Tazaki .
4,699,356 10/1987 Hargrove .
4,700,202 10/1987 Kuranishi .
4,700,205 10/1987 Rich .
4,700,744 10/1987 Rutter .
4,709,725 12/1987 Morrison .
4,714,937 12/1987 Kaplinsky .
4,719,475 1/1988 Kiyohara .
4,734,711 3/1988 Piatt .
4,736,774 4/1988 Vonasek .
4,737,801 4/1988 Ichihashi .

| | | | |
|---|---|---|---|
| 4,739,347 | 4/1988 | Ishikawa . | |
| 4,739,847 | 4/1988 | Terasawa . | |
| 4,757,331 | 7/1988 | Mizusawa . | |
| 4,760,409 | 7/1988 | Kiyohara . | |
| 4,765,657 | 8/1988 | Cruse . | |
| 4,775,871 | 10/1988 | Abe . | |
| 4,777,497 | 10/1988 | Nozu . | |
| 4,785,314 | 11/1988 | Terasawa . | |
| 4,811,035 | 3/1989 | Huliba . | |
| 4,814,786 | 3/1989 | Hoisington . | |
| 4,814,794 | 3/1989 | Sato . | |
| 4,825,228 | 4/1989 | Gloeckler . | |
| 4,826,052 | 5/1989 | Micallef . | |
| 4,831,389 | 5/1989 | Chan . | |
| 4,844,408 | 7/1989 | Beaston . | |
| 4,849,773 | 7/1989 | Owatari . | |
| 4,853,708 | 8/1989 | Walters . | |
| 4,881,569 | 11/1989 | Fournier . | |
| 4,888,602 | 12/1989 | Watanabe . | |
| 4,896,171 | 1/1990 | Ito . | |
| 4,898,209 | 2/1990 | Zbed . | |
| 4,907,019 | 3/1990 | Stephens . | |
| 4,910,529 | 3/1990 | Regnault . | |
| 4,911,203 | 3/1990 | Garms . | |
| 4,920,360 | 4/1990 | Terasawa . | |
| 4,926,196 | 5/1990 | Mizoguchi . | |
| 4,928,126 | 5/1990 | Asai . | |
| 4,929,109 | 5/1990 | Ikenaga . | |
| 4,931,044 | 6/1990 | Beiter . | |
| 4,931,814 | 6/1990 | Yoshimura . | |
| 4,934,655 | 6/1990 | Blenkush . | |
| 4,935,751 | 6/1990 | Hamlin . | |
| 4,940,995 | 7/1990 | Hine . | |
| 4,940,997 | 7/1990 | Hamlin et al. . | |
| 4,942,901 | 7/1990 | Vescovini . | |
| 4,953,756 | 9/1990 | Breault . | |
| 4,957,483 | 9/1990 | Gonser . | |
| 4,958,754 | 9/1990 | Dennis . | |
| 4,959,667 | 9/1990 | Kaplinsky . | |
| 4,961,082 | 10/1990 | Hoisington . | |
| 4,967,207 | 10/1990 | Ruder . | |
| 4,968,998 | 11/1990 | Allen . | |
| 4,970,533 | 11/1990 | Saito . | |
| 4,973,993 | 11/1990 | Allen . | |
| 4,977,413 | 12/1990 | Yamanaka . | |
| 4,987,429 | 1/1991 | Finley . | |
| 4,991,820 | 2/1991 | Kohn . | |
| 4,992,802 | 2/1991 | Dion . | |
| 4,995,940 | 2/1991 | Hine . | |
| 4,999,652 | 3/1991 | Chan . | |
| 5,002,254 | 3/1991 | Belisaire . | |
| 5,008,688 | 4/1991 | Ebinuma . | |
| 5,025,270 | 6/1991 | Umezawa . | |
| 5,026,024 | 6/1991 | Ito . | |
| 5,030,973 | 7/1991 | Nonoyama . | |
| 5,043,746 | 8/1991 | Abe . | |
| 5,053,787 | 10/1991 | Terasawa . | |
| 5,070,347 | 12/1991 | Yuki . | |
| 5,074,524 | 12/1991 | Wade . | |
| 5,098,385 | 3/1992 | Walsh . | |
| 5,100,394 | 3/1992 | Dudar et al. . | |
| 5,119,115 | 6/1992 | Buat . | |
| 5,126,767 | 6/1992 | Asai | 346/140 R |
| 5,135,489 | 8/1992 | Jepson et al. | 604/48 |
| 5,136,305 | 8/1992 | Ims . | |
| 5,136,309 | 8/1992 | Iida . | |
| 5,153,612 | 10/1992 | Dunn . | |
| 5,155,502 | 10/1992 | Kimura . | |
| 5,158,554 | 10/1992 | Jepson et al. . | |
| 5,159,348 | 10/1992 | Dietl . | |
| 5,167,648 | 12/1992 | Jepson et al. . | |
| 5,182,581 | 1/1993 | Kashimura . | |
| 5,187,498 | 2/1993 | Burger . | |
| 5,188,620 | 2/1993 | Jepson et al. . | |
| 5,189,438 | 2/1993 | Hine . | |
| 5,199,470 | 4/1993 | Goldman . | |
| 5,206,668 | 4/1993 | Lo et al. . | |
| 5,211,638 | 5/1993 | Dudar et al. . | |
| 5,215,231 | 6/1993 | Paczonay . | |
| 5,215,537 | 6/1993 | Lynn et al. . | |
| 5,216,452 | 6/1993 | Suzuki . | |
| 5,220,345 | 6/1993 | Hirosawa . | |
| 5,221,935 | 6/1993 | Uzita . | |
| 5,221,936 | 6/1993 | Saito . | |
| 5,232,109 | 8/1993 | Tirrell et al. . | |
| 5,242,393 | 9/1993 | Brimhall et al. . | |
| 5,245,915 | 9/1993 | Ford . | |
| 5,255,827 | 10/1993 | Breault . | |
| 5,270,739 | 12/1993 | Kitani . | |
| 5,280,300 | 1/1994 | Fong . | |
| 5,283,593 | 2/1994 | Wehl . | |
| 5,289,212 | 2/1994 | Carlotta . | |
| 5,293,913 | 3/1994 | Preszler . | |
| 5,305,920 | 4/1994 | Reiboldt . | |
| 5,306,125 | 4/1994 | Weag . | |
| 5,307,091 | 4/1994 | DeCoste, Jr. . | |
| 5,311,214 | 5/1994 | Hirasawa . | |
| 5,320,326 | 6/1994 | Ju . | |
| 5,328,055 | 7/1994 | Battle . | |
| 5,329,294 | 7/1994 | Ontawar . | |
| 5,331,339 | 7/1994 | Takahashi . | |
| 5,337,925 | 8/1994 | Ferrara, Jr. . | |
| 5,341,161 | 8/1994 | Yamakawa . | |
| 5,343,226 | 8/1994 | Niedermeyeyr . | |
| 5,348,192 | 9/1994 | Sardynski . | |
| 5,351,073 | 9/1994 | Kageyama . | |
| 5,351,383 | 10/1994 | Behnke et al. . | |
| 5,354,275 | 10/1994 | Behnke et al. . | |
| 5,359,353 | 10/1994 | Hunt . | |
| 5,359,356 | 10/1994 | Ecklund . | |
| 5,359,357 | 10/1994 | Takaki . | |
| 5,365,260 | 11/1994 | Kitani . | |
| 5,365,262 | 11/1994 | Hattori . | |
| 5,368,070 | 11/1994 | Bosley . | |
| 5,369,429 | 11/1994 | Erickson . | |
| 5,372,306 | 12/1994 | Yianilos . | |
| 5,381,172 | 1/1995 | Ujita . | |
| 5,385,331 | 1/1995 | Allread . | |
| 5,390,702 | 2/1995 | Smith, III . | |
| 5,394,177 | 2/1995 | McCann . | |
| 5,396,268 | 3/1995 | Mader . | |
| 5,400,066 | 3/1995 | Matsumoto . | |
| 5,400,573 | 3/1995 | Crystal . | |
| 5,402,982 | 4/1995 | Atkinson . | |
| 5,403,293 | 4/1995 | Grabenkort . | |
| 5,406,320 | 4/1995 | Durst . | |
| 5,408,256 | 4/1995 | Keen . | |
| 5,426,459 | 6/1995 | Kaplinsky . | |

FLUID INTERCONNECT FOR INK-JET PEN

TECHNICAL FIELD

This invention relates to a fluid interconnect that can be used to connect a pen on an ink-jet printer to an ink delivery tube.

BACKGROUND AND SUMMARY OF THE INVENTION

An ink-jet printer typically has a pen mounted to a carriage that traverses a printing surface, such as a piece of paper. The pen includes a print head that is controlled to selectively eject tiny droplets of ink onto the printing surface to form desired images and characters. The pen also typically includes pressure regulating mechanisms to maintain the ink at an appropriate pressure for use by the print head.

To work properly, such a printer must have a reliable supply of ink for the print head. One type of printer uses an ink supply container that is separate from the pen. The separate ink container is stationary and is generally located near the reciprocating carriage and pen on the printer.

An ink delivery tube connects the ink container to the carriage. Ink is delivered to the pen under pressure. The carriage provides a stable housing for the delivery tube. The pen is coupled to the housing and connected to the delivery tube.

A well-sealed fluid interconnect at the carriage between the delivery tube and the pen is necessary to prevent leaks that may damage the printer. In addition, the fluid interconnect should prevent ink from escaping when the pen is uncoupled from the carriage housing so that no ink comes in contact with the user.

In printers having stationary ink containers, one pen can last through many ink supplies. Eventually, though, the ink pen must be replaced. Therefore, it is desirable that the seals of the fluid interconnect remain robust over long periods of engagement with the pen and not fail as a result of very long engagement times.

It is also desirable that the pen be replaceable without depressurizing the delivery tube.

The present invention provides a well-sealed fluid interconnect between an ink pen and a carriage. The fluid interconnect maintains a tight seal during insertion, engagement, and extraction of the pen. The interconnect reseals tightly, even after very long engagement periods.

As another aspect of this invention, the part of the pen that contributes to the fluid interconnect includes a cap with a ridge that attracts ink that may escape from the interconnect. The cap also prevents the escaped ink from contacting the printer or the user.

DESCRIPTION OF PREFERRED EMBODIMENT

Figure 1:
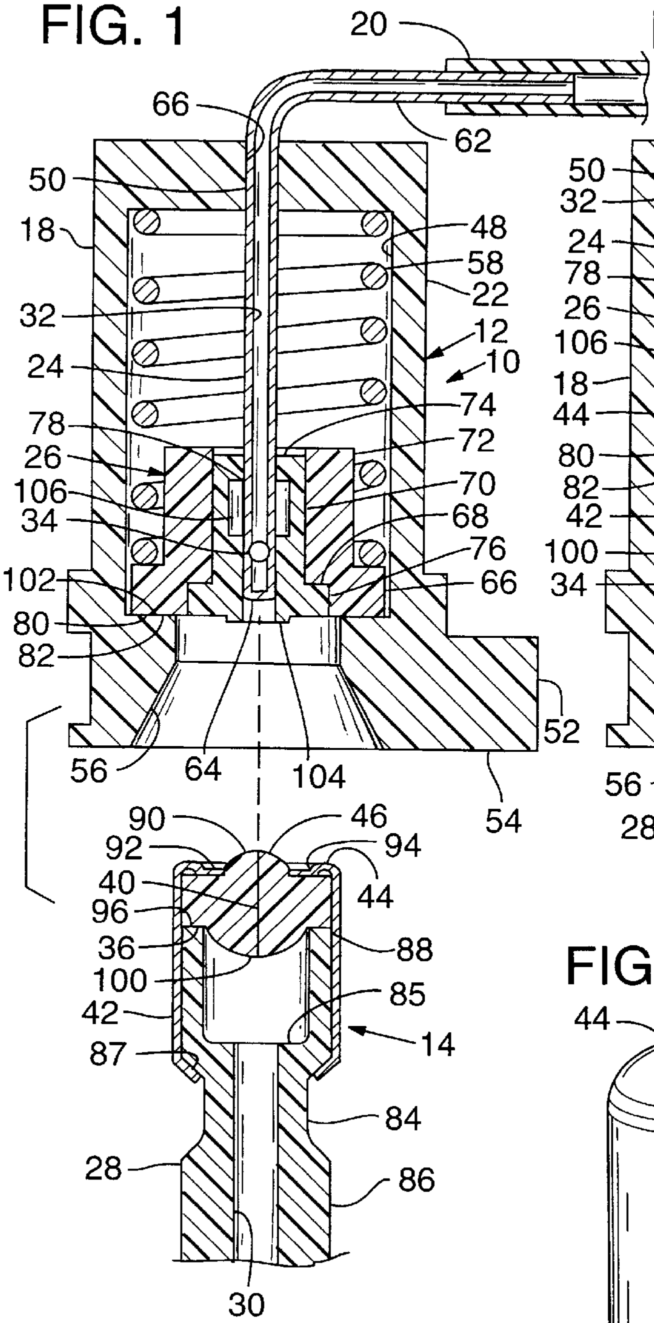
FIG. 1 is a cross-sectional view of a fluid interconnect of the present invention in a closed, uncoupled position.
Figure 4:
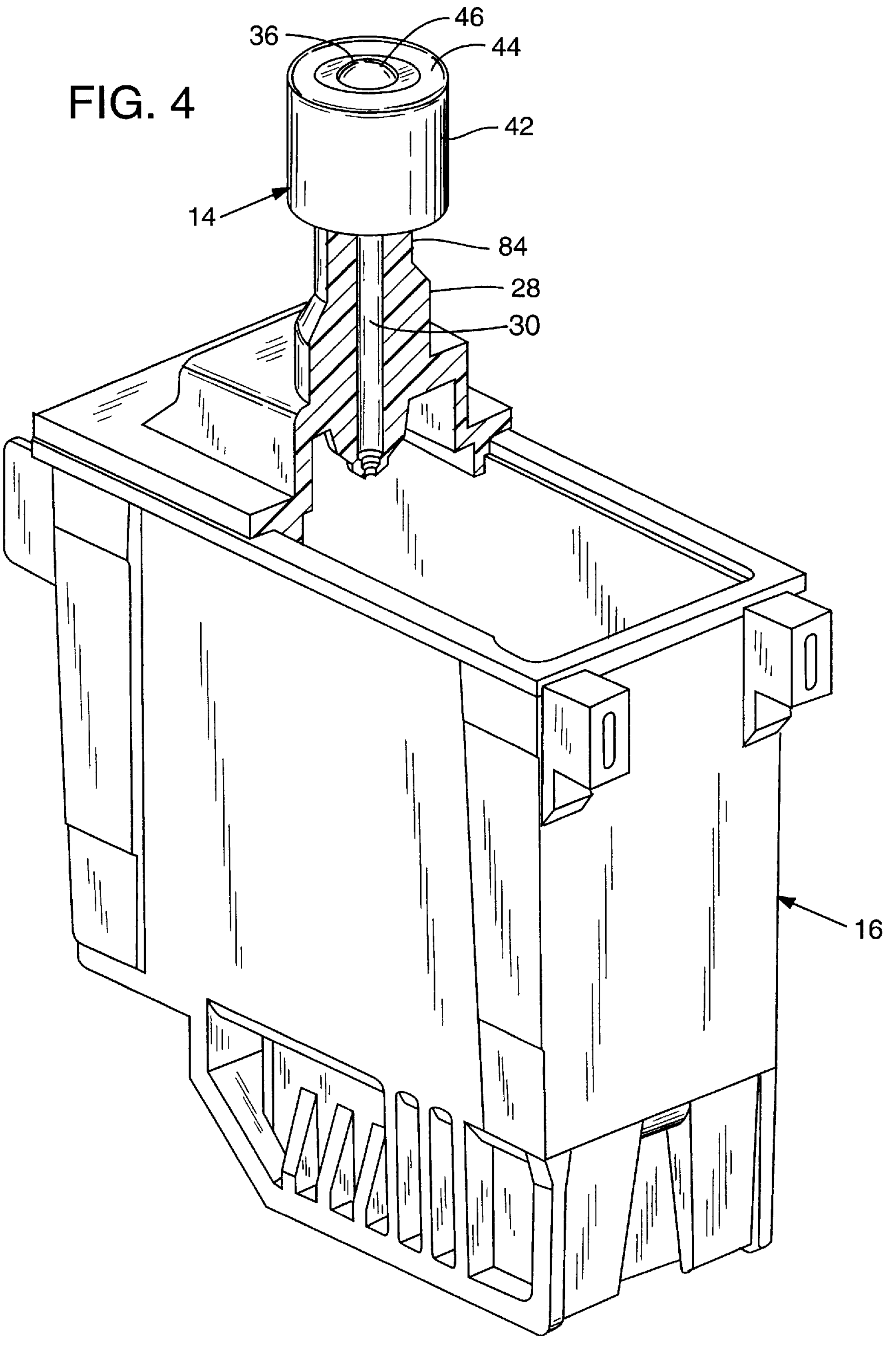
FIG. 4 is a perspective view of an ink pen that carries the inlet assembly in accordance with the present invention.

A fluid interconnect 10 in accordance with the present invention is illustrated in FIG. 1. The fluid interconnect 10 connects an ink delivery tube 20 to an ink pen 16, a portion of which is shown in FIG. 4, that is coupled to a carriage 18, a portion of which is shown in FIG. 1. The illustrated fluid interconnect 10 includes an outlet assembly 12 incorporated into the carriage 18, and an inlet assembly 14 carried on the pen 16. The carriage has features that engage and support the pen 16 for reciprocating movement within the printer (not shown), with the flexible tube 20 trailing between the pen 16 and a remote ink supply.

The outlet assembly 12 includes a housing 22, an elongated needle 24, and a collar 26. The housing 22 is cylindrical with a hollow interior 48 and a flange 52 at the bottom end 54. The bottom end 54 also has a countersunk hole 56 leading to the hollow interior 48 of the housing 22. The upper end 60 of the housing 22 has an axial hole 50 through which the needle 24 enters the housing 22.

The needle 24 is an L-shaped rigid member, preferably 18-gauge stainless steel, in the vicinity of the housing 22. The outer end of the needle 24 is joined to the flexible ink tube 20, which is in fluid communication with an ink supply container (not shown). The needle 24 extends axially along the length of the interior 48 of the housing 22 and does not move relative to the housing 22. The needle 24 has a diameter of about 1.2 mm, including an axial bore 32 extending therethrough and terminating in a lateral hole 34 at the blunt inner end 64 of the needle 24. Ink from the supply container flows through the tube 20, into the bore 32 of the needle 24 and out of the lateral hole 34 when that hole is uncovered, as will be explained.

The collar 26 includes a rigid plastic outer portion 72 and a compliant inner portion 74, also referred to as a humidor. The rigid outer portion 72 is a hollow cylinder having a flange 66 extending radially therefrom at one end. An annular recess 68 is cut out from the inside 70 of the collar 26 at the flanged end.

The compliant inner portion 74 is shaped and sized such that it fits tightly inside of the rigid outer portion 72. To this end, the compliant portion 74 is cylindrical in shape with a compliant flange 76 that fits within the recess 68. The compliant portion 74 has an axial channel 78 through which the needle 24 extends.

The channel 78 of the compliant portion 74 is shaped to include an annular pocket 106, which is spaced away from the flanged end of the compliant portion 74. The pocket 106 has a larger diameter than that of the needle 24, thereby to reduce the overall contact area between the compliant portion 74 and the needle 24 when the collar is slid along the needle 24 as described below.

The face of the compliant inner portion 74 has an integrally formed, cylindrical boss 104 extending axially downward therefrom. The boss 104 minimizes the contact area between the outlet and inlet assemblies 12 and 14 to provide a robust seal, as will be explained below. The compliant portion 74 preferably is made of ethylene propylene dimer monomer (although other, similar elastomers could be used) that fits tightly around the needle 24.

The collar 26 and compliant portion 74 move together along the length of the needle 24. The collar 26 is biased toward the lower end of the housing 22 toward a "closed" position by a spring 58. The spring 58 is compressed between the upper wall of the housing interior 48 and the collar flange 66. In the closed position, the face 80 of the collar 26 (that is, the continuous surface defined by both the rigid portion 72 and compliant portion 74) is flush with the bottom inner surface 102 of the housing interior 48. The closed position of the collar 26 locates the walls of the channel 78 to cover the lateral hole 34 in the needle 24 to occlude ink flow therefrom, as shown in FIG. 1.

Figure 2:
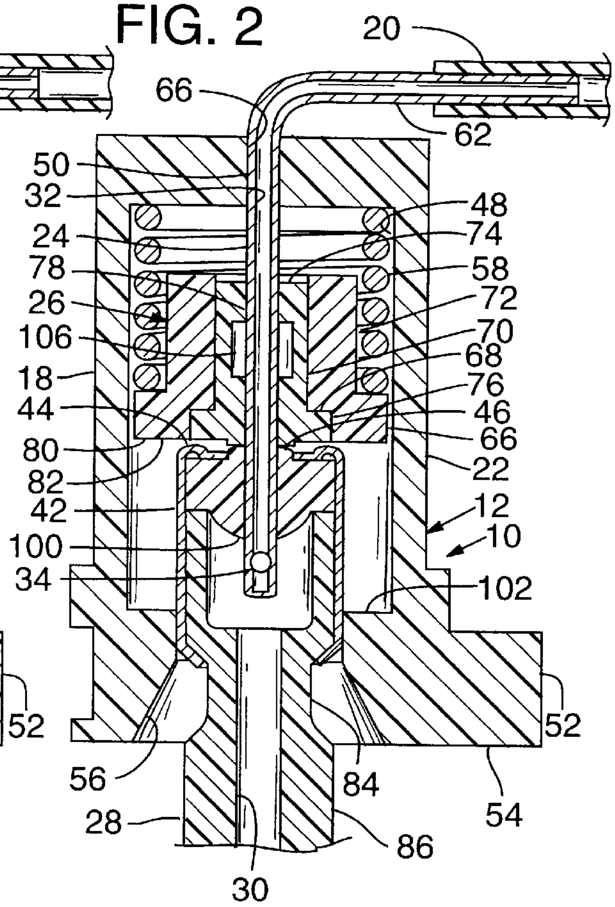
FIG. 2 is a cross-sectional view, like FIG. 2, but with the interconnect in an open, coupled position.

The collar 26 is movable upwardly by the inlet assembly 14 into an "open" position in which the collar 26 slides axially upward along the needle 24 to uncover the lateral hole 34, as shown in FIG. 2. In the open position, ink can flow from the outlet assembly 12, as will be discussed in greater detail below.

The inlet assembly 14 is preferably mounted to protrude from the top of an ink-jet pen 16, as shown in FIG. 4, that is coupled to the carriage housing 22. The assembly 14 includes a fitment 28, a septum 36, and a cap 42. The fitment 28 is preferably rigid plastic, such as polysulfone, and is integrally formed with or otherwise attached to the pen 16.

The fitment 28 is cylindrical and has near its midsection a neck 84. The neck 84 has a smaller diameter than the top 88 and bottom 86 of the fitment 28. The tapered part of the neck 84 provides an undersurface 87 against which the cap 42 is crimped to the fitment 28 as will be explained below.

The fitment 28 also has an axial passage 30 preferably having a large diameter at the top 88 of the fitment 28 with a sudden reduction in diameter at shoulder 85 near the junction of the neck 84 and top 88. The passage 30 is in fluid communication with the interior of the ink pen 16, as shown in FIG. 4.

The septum 36 of the inlet assembly is generally cylindrical and fits onto the top 88 of the fitment 28. The outer diameter of the septum 36 is slightly larger than the outer diameter of the top of the fitment 28. In the illustrated embodiment, the septum 36 has a diameter of 3 millimeters and is made of 35 durometer synthetic polyisoprene that is materially cured for about 240 seconds at 330 degrees Fahrenheit. Smaller septums (e.g., having a 2.5 mm diameter) could be used, although such septums would be made with a correspondingly reduced cure time. The proper cure time provides the septum 36 with a sufficiently high crosslink density and makes the septum 36 resistant to compression setting, the significance of which is explained below.

Figure 3:
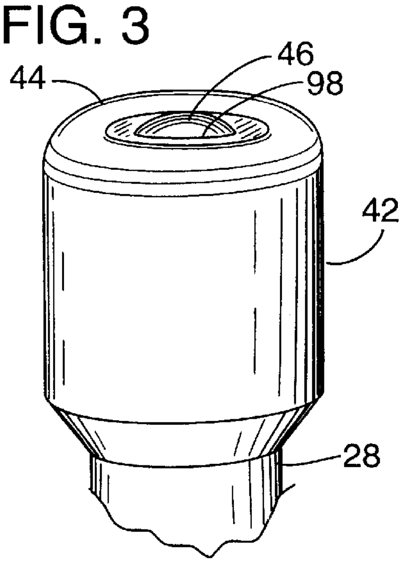
FIG. 3 is a detail perspective view of the cap and the septum on an inlet assembly component of the present invention.

The cap 42 surrounds the septum 36 and top 88 of the fitment 28. The cap 42 has a slightly smaller inner diameter than the septum 36 outer diameter so that the septum 36 fits snugly within the cap 42. The cap 42 is a thin-walled, generally cylindrical member with a top surface 92 that extends radially inward but does not completely enclose the top of the septum 36. Rather, the top surface 92 has a central top hole 98, as best seen in FIG. 3. The top hole 98 has approximately the same diameter as the boss 104 on the inner portion 74 of the collar 26.

In the illustrated embodiment, the cap 42 is formed by drawing a circular aluminum plate of about 0.4 mm thickness over a die. Once the cap 42 is formed, the top hole 98 is punched into the cap 42.

The cap 42 is crimped onto the fitment 28, by axially pressing the cap 42 downward and bending the bottom portion of the cap 42 around the tapered undersurface 87 of the fitment 28. The crimping causes compression of the septum 36. Crimping the cap 42 onto the fitment 28 axially compresses the septum 36, causing the septum 36 to deform axially to form a blister 46 that bulges through the top hole 98 in the cap 42, as shown in FIGS. 1–3. A similar bulge 100 in the underside of the septum 36 protrudes into the fitment passage 30.

The size of the blister 46 is controlled by the amount of axial and radial compression exerted on the septum 36 by the cap 42. In the illustrated embodiment, the cap 42 subjects the septum 36 to about eight percent axial compression and five percent radial compression, which results in a blister height of approximately 0.6 millimeters above the top surface 92 of the cap 42.

The cap 42 is shaped to include a ridge 44 projecting from the perimeter of the top surface 92 of the cap 42, as shown in FIGS. 1–3. The ridge 44 is formed by a final reverse draw in the cap forming process. The reverse draw is accomplished by depressing a die on the top surface 92 of the cap 42. The die has a smaller diameter than the die used to form the cap 42. Thus, only the area of the top surface 92 under the die is depressed, leaving the ridge 44 elevated from the top surface 92. The cap 42 has a sharp corner 94 where the ridge 44 joins with the top surface 92 of the cap 42 (See FIG. 1). The sharp corner 94 defines a space that attracts by capillarity any ink that may leak from the inlet assembly 14. The ridge 44 confines the ink to the corner 94 of the top surface 92 of the cap 42 and thus minimizes exposure of the ink to the user. The ridge 44 also increases the stiffness of the cap 42, making the cap 42 more resistant to deformation from inadvertent impacts, such as when a pen is dropped.

After the cap 42 is crimped onto the fitment 28, the septum 36, including the blister 46 and the bulge 100, is slit to form a normally closed slit 40 for receiving the needle 24 of the outlet assembly 12. The slit 40 may be made with any sharp blade, such as a carbide knife or an x-acto blade. Alternatively, the slit 40 could be molded into the septum 36, in which case compressing the cap 42 on the septum 36 would close the slit 40.

When the inlet assembly 14 is disengaged from the outlet assembly 12, as shown in FIG. 1, the slit 40 in the septum 36 is closed so that no ink from the passage 30 can be released from the inlet assembly 14 through the slit 40. When the inlet assembly 14 is inserted into the outlet assembly 12, the slit 40 is forced open by the needle 24 on the outlet assembly 12, as described next.

To make a robust, sealed connection, the inlet assembly 14 is inserted upwardly into the countersunk hole 56 on the outlet assembly 12. The outermost part of the countersunk hole 56 is tapered to align the slit 40 with the needle 24. The blister 46 on the septum 36 of the inlet assembly 14 contacts and deforms slightly against the boss 104 of the compliant portion 74 of the collar 26 to form a tight, axial, face seal between the inlet assembly 14 and the outlet assembly 12. The protruding boss 104 helps accomplish this tight face seal by providing a relatively small volume of compliant material exposed for contact with the blister, which volume readily deforms to seal tightly to the blister.

As the inlet assembly 14 is further inserted into the outlet assembly 12, the blister 46 of the septum 36 continues to press on the boss 104 of the collar 26 to overcome the force of the spring 58 and push the collar 24 from its closed position, as shown in FIG. 1, upward along the axis of the needle 24 to the open position, as shown in FIG. 2.

As the collar 26 slides from the closed position to the open position, the blunt end 64 of the needle 24 penetrates the slit 40 in the blister 46 and extends through the septum 36 until the lateral hole 34 is fully exposed. In the open position, the lateral hole 34 on the needle 24 is exposed within the passage 30 on the inlet assembly 14 to establish fluid communication between the remote ink container and the pen 16. Thus, ink can flow from the ink container, through the tube 20, into the axial bore 32 in the needle 24, through the tube 20, through the lateral hole 34 into the passage 30, and into the ink pen 16.

As noted earlier, the pocket 106 in the collar 26 reduces the contact area between the compliant portion 74 and the needle 24. As a result, the spring constant of the spring 58 can be smaller than what would be required in the absence of the pocket, and still have sufficient force to overcome friction between the needle 24 and the compliant portion 74 to return the collar 26 back to the closed position after the inlet assembly 14 has been extracted from the outlet assembly 12, as will be explained. Similarly, a lower spring constant reduces the insertion force required for inserting the inlet assembly 14 into the outlet assembly 12 to move the collar 26 from a closed position to an open position, as will be explained next.

In a preferred embodiment, the ink pen 16 to which the inlet assembly 14 is attached is supported in the carriage 18 in a manner that allows engagement and disengagement of the inlet assembly 14 and that supports the inlet assembly 14 and outlet assembly 12 in the open position (FIG. 2). It will be appreciated that any of a number of mechanisms can be used to support the pen on the carriage.

When the inlet assembly 14 is to be disconnected from the outlet assembly 12 (for example, to replace the pen), the inlet assembly 14 is extracted (pulled downwardly) from the outlet assembly 12, and the spring 58 forces the collar 26 back into the closed position, in which the walls of the channel 78 cover the lateral hole 34 in the needle 24 to occlude ink flow from the bore 32. Also, as the inlet assembly 14 is disengaged from the outlet assembly 12, the slit 40 in the septum 36 returns to the closed position to occlude ink flow from the passage 30 in the fitment 28.

The material of the septum 36 and the compressive forces exerted on the septum 36 by the cap 42 help ensure that the slit 40 will close tightly even after the needle 24 of the inlet assembly 14 has been inserted in the outlet assembly 12 for lengthy periods. Also, as a result of the optimized cure time of the septum, the force required for inserting the needle 24 into the septum is minimized. A small-diameter needle also helps ensure that the slit 40 will reseal after long engagement periods.

If any ink were to escape from the fluid interconnect 10 during disengagement, the ink would be attracted by capillarity to the sharp corner 94 on the ridge 44. In that location, the ink is least likely to be seen or contacted by a user.

It is notable that the lateral hole in the needle is not exposed to ambient air during insertion or extraction or while disengaged. The lateral hole is sealed radially by the walls of the channel 78 in the inner compliant portion 74 of the septum 36 while the collar 26 is closed, is sealed axially by the face seal between the boss 104 and the blister 46 during insertion and extraction, is sealed radially by the slit 40 in the septum 36 once the outlet assembly 12 is inserted into the inlet assembly 14, and is exposed only once it is inside the passage 30 of the inlet assembly 14. It will be appreciated, therefore, that the ink within the delivery tube 20 need not be drained or depressurized during the disconnection and reconnection of the inlet and outlet assemblies.

This description illustrates various embodiments of the present invention and should not be construed to limit the scope thereof in any way. Other modifications and variations may be made to the assembly described without departing from the invention as defined by the appended claims and their equivalents. For example, it is contemplated that the septum 36 could be formed of other compliant material, such as natural rubber, and need not be slit. Further, plastic swaging or welding could be used to fasten the cap to the fitment.

The invention claimed is:

1. A fluid interconnect for connecting an ink supply to an ink-jet pen, the fluid interconnect comprising:

an outlet assembly comprising:

a housing;

an elongated needle having a first end inside the housing and a second end connectable to an ink container, the needle having an axial bore that terminates near the first end and is contiguous with a lateral hole in the needle; and a collar positioned on the needle, the collar being movable into a closed position in which the collar covers the lateral hole to occlude fluid flow through the needle, the collar also being movable into an open position in which the collar is away from the lateral hole; and an inlet assembly comprising:

a fitment having a passage for fluid flow, the fitment being insertable into the housing; and a penetrable septum mounted to the fitment, the septum being penetrated by the first end of the needle as the fitment is inserted into the housing, the septum contacting the collar to move the collar from the closed position to the open position, in which the lateral hole is exposed within the passage.

2. The fluid interconnect of claim 1 in which the septum is a compressed member that occludes the fitment passage unless penetrated by the first end of the needle.

3. The fluid interconnect of claim 2 in which the inlet assembly includes a cap that attaches to the fitment, the cap being sized and arranged to compress the septum.

4. The fluid interconnect of claim 3 in which the cap is made of metal.

5. The fluid interconnect of claim 3 in which the cap includes a ridge that defines a capillary space for attracting ink.

6. The fluid interconnect of claim 3 in which the septum is compressed in a manner that creates a blister in a surface of the septum through which blister the needle penetrates.

7. The fluid interconnect of claim 6 wherein the collar has a face that abuts the blister of the septum as the septum moves into contact with the collar.

8. The fluid interconnect of claim 7 in which the collar face includes a protruding boss for contact with the blister of the septum.

9. The fluid interconnect of claim 8 in which the boss diameter is about equal to the diameter of the blister on the septum.

10. The fluid interconnect of claim 1 in which the septum is made of cured polyisoprene.

11. The fluid interconnect of claim 1 in which the first end of the needle is blunt.

12. A connector for use in an ink-jet printer having an ink tube connected to an ink container, the connector comprising:

a housing;

an elongated needle having a first end inside the housing and a second end connectable to the ink tube, the needle having an axial bore that terminates near the first end and is contiguous with a lateral hole in the needle; and a collar positioned on the needle, the collar being movable relative to the needle between a closed position in which the collar covers the lateral hole to occlude fluid flow through the needle and an open position in which the collar is away from the lateral hole.

13. The connector of claim 12 including a spring for urging the collar toward the closed position.

14. A method of manufacturing a sealed connector having an exposed surface for engagement with a second surface on another connector, the method comprising the step of compressing a septum within a cap having a top surface with a hole formed in the top surface such that a part of the septum is deformed into a blister on the exposed surface that projects above the top surface through the hole.

15. The method of claim 14 further comprising the step of slitting the septum through the blister to form a slit for receiving a needle member.

16. A fluid inlet assembly for an ink-jet pen, the inlet assembly comprising:

a fitment mounted to the pen and having an ink passage therein;

a septum mounted to the fitment for sealing the passage;

a cap having a top surface with a hole formed in the top surface that surrounds and compresses the septum such that a blister is formed in the septum that projects above the top surface through the hole.

17. The inlet assembly of claim 16 in which the blister is slit to open when a needle member is penetrated through the septum.

18. The inlet assembly of claim 16 in which the cap is made of a metal.

19. The inlet assembly of claim 16 in which the cap has a ridge that projects above the top surface to define a junction wherein a space on the cap is defined for attracting by capillarity ink that may be present on the cap.

20. The inlet assembly of claim 16 in which the septum is made of cured polyisoprene.

21. A cap for compressing a penetrable septum of a connector fitment, the cap having a top surface and a hole formed in the top surface, the cap being deformed around the fitment thereby to compress the septum such that a blister is formed in the septum that projects above the top surface through the hole.

22. The cap of claim 21 including a ridge formed therein that projects above the top surface to define a junction wherein a capillary space is defined for attracting liquid that is present on the cap.

* * * * *